United States Patent
Stainsby et al.

(10) Patent No.: US 6,704,593 B2
(45) Date of Patent: Mar. 9, 2004

(54) REALTIME MR SCAN PRESCRIPTION USING PHYSIOLOGICAL INFORMATION

(75) Inventors: Jeff Stainsby, Thornhill (CA); Marshall S. Sussman, Toronto (CA); Graham A. Wright, Toronto (CA); Tzvi Goldman, Thornhill (CA)

(73) Assignee: Sunnybrook & Women's College Health Centre, Ontario (CA)

( * ) Notice: Subject to any disclaimer, the term of this patent is extended or adjusted under 35 U.S.C. 154(b) by 303 days.

(21) Appl. No.: 09/837,299

(22) Filed: Apr. 19, 2001

(65) Prior Publication Data

US 2002/0156366 A1 Oct. 24, 2002

(51) Int. Cl.$^7$ ................................................. A61B 5/05
(52) U.S. Cl. ..................................................... 600/413
(58) Field of Search ................................. 600/413, 410, 600/414, 415; 324/307, 308, 309

(56) References Cited

U.S. PATENT DOCUMENTS

| | | | | |
|---|---|---|---|---|
| 5,251,628 A | * | 10/1993 | Foo | 600/413 |
| 5,435,303 A | * | 7/1995 | Bernstein et al. | 600/413 |
| 5,541,512 A | | 7/1996 | Dumoulin et al. | |
| 5,905,377 A | | 5/1999 | Kerr et al. | |
| 5,997,883 A | * | 12/1999 | Epstein et al. | 324/306 |
| 6,067,465 A | | 5/2000 | Foo et al. | |
| 6,184,682 B1 | | 2/2001 | Ehman et al. | |
| 6,198,959 B1 | | 3/2001 | Wang | |
| 6,201,393 B1 | | 3/2001 | Bernstein et al. | |
| 6,246,897 B1 | * | 6/2001 | Foo et al. | 600/413 |

OTHER PUBLICATIONS

Brittain, J., et.al., Magnetic Resonance In Motion, vol. 33, p. 689, 1995.

Foltz, W., et.al., Magnetic Resonance in Motion, vol. 38, p. 759, 1997.

Hardy, C.J., Magnetic Resonance in Medicine, vol. 40, pp. 105–111, 1998.

Kerr, A., et.al., Magnetic Resonance In Motion, vol. 38, p. 355, 1997.

Meyer, C.H., et al. Proceedings, 5th meeting, ISMRM, Vancouver, p. 439, 1997.

Riederer, S., et.al., Magnetic Resonance In Motion, vol. 8, p. 1, 1988.

Sachs, T.S., et.al., Magnetic Resonance In Motion, vol. 34, p. 412, 1995.

Sussman, M., et.al., 7th Proceeding, ISMRM, p. 1267, 1999.

Wright, RC, et.al., Magnetic Resonance In Medicine, vol. 12, pp. 407–415, 1989.

(List continued on next page.)

*Primary Examiner*—Daniel Robinson
(74) *Attorney, Agent, or Firm*—Miles & Stockbridge P.C.; Edward J. Kondracki

(57) ABSTRACT

Realtime magnetic resonance imaging (MRI) uses cardiac and respiratory monitoring tools to avoid or minimize motion-induced image artifacts. A series of initial MR images are associated with the physiological data from the cardiac, respiratory, or other monitoring tools. The tools provide physiological data in conjunction with anatomic or spatial information such that the optimal gating times (i.e., for acquiring MR image data) in the cardiac and respiratory cycles can be identified and the optimal acquisition durations are identified relative to the physiological data. The process then uses MRI with the identified optimal gating times and acquisition durations to produce a high quality output image of the anatomy of interest. The high quality image can be one or more of the following: a two-dimensional (2D) with a higher signal-to-noise ratio (i.e., higher than the initial MR images), a 2D image with higher spatial resolution, and a three-dimensional (3D) image,

20 Claims, 5 Drawing Sheets

OTHER PUBLICATIONS

Yang, P.C., et.al., Journal of the American College of Cardiology, vol. 32,(7), pp. 2049–2056, 1998.

Stainsby, Jeffrey A., et al., "Realtime MR with Physiological Monitoring for Improved Scan Localization".

"A New Anterior Cardiac Phased Array Coil for High–Resolution Coronary Artery Imaging".

Hardy, Christopher J., et al., "Coronary Angiography by Real–Time MRI with Adaptive Averaging," Magnetic Resonance in Medicine 44:940–946, 2000.

Sussman, Marshall S. et al., "Non–ECG–Triggered, High–Resolution, Coronary Artery Imaging using Adaptive Averaging with Real–Time Variable–Density Spirals,".

* cited by examiner

REALTIME MR SCAN PRESCRIPTION USING PHYSIOLOGICAL INFORMATION

BACKGROUND OF THE INVENTION

The field of the invention is nuclear magnetic resonance imaging (MRI) methods and systems. More particularly, the invention relates to the reduction of image artifacts caused by patient motion during an MRI scan by determining a scan prescription using physiological information.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "dipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

Typical magnetic resonance exams can be divided into two broad stages: localization and information gathering. In the information gathering stage, specific scan prescriptions are utilized to obtain the required clinical information. The localization stage is generally less well-defined and is needed simply to determine the appropriate location and timing of the subsequent information gathering stage. In areas where there is significant motion due to cardiac contractions and respiration, this timing and localization is critical as the area of interest may move out of the prescribed scan location in portions of the cardiac or respiratory cycles. Also, motion during the acquisition of data can cause significant artifacts in the resultant MR images.

The challenges of scanning in and around the heart in the presence of cardiac and respiratory motion are well known. For 2D scanning techniques it is essential to localize not just to a particular spatial location, but also to an exact cardiac and respiratory phase as the structures of interest may move out of the scan plane during either physiological cycle. For 3D imaging it is advantageous to have structures of interest in-plane since through-plane resolution is typically poorer. In addition, due to the relatively long scan times required for 3D vs. 2D scans, it is advantageous to scan for as long a portion of the cardiac cycle as possible for greater scan efficiency. Erroneous timing can result in significant motion during the acquisition resulting in a degradation of image quality.

Conventional magnetic resonance imaging in and around the heart has often used some form of cardiac and respiratory compensation or gating to synthesize an image at specific phases of the cardiac and/or respiratory cycles from data acquired over multiple heart beats and respiratory cycles. This methodology not only has the potential for error due to inconsistencies between cycles, but can take a long time and only produces images for a limited number of spatial locations and points within either the cardiac or respiratory cycles.

Realtime or fluoroscopic MRI is a technique that allows imaging to occur at rates up to 20-30 frames per second. In certain situations, realtime MRI has the potential to be used for both the localization and the information gathering stages. However, in many applications a subsequent imaging series is still desired. In this situation realtime MRI has the potential to provide rapid localization of the desired spatial position in any arbitrary scan plan and this localization information can be used in the subsequent scan.

Acquiring magnetic resonance (MR) images may require a time period of seconds to minutes. Over this period, significant anatomical motion may occur—specifically, cardiac- and respiratory-induced motion. This motion produces artifacts that may significantly degrade image quality. A number of different techniques have been developed in order to compensate for the effects of this motion. These techniques attempt to either acquire data during periods of minimal motion, or to correct for the effects of motion when it does occur. For these techniques to compensate for the effects of motion, the motion itself must be known accurately throughout the data acquisition. In the past, bellows and navigator echoes placed on the diaphragm have been used to determine respiratory-induced motion. A shortcoming of this approach is that the relationship between diaphragm position and respiratory-induced motion at anatomy remote from the diaphragm will vary from patient to patient and across studies. For cardiac-induced motion, ECG-waveforms have been used. The problem with ECG waveforms is that there may be substantial variation across patients and across studies. A drawback with some previous motion compensation techniques is that they assume that one patient's anatomy is best viewed at the same part of the cardiac cycle (or respiratory cycle) as was used to view the same feature on the previous patient.

BRIEF SUMMARY OF THE INVENTION

The present method and system identifies the proper position and timing to use for a magnetic resonance scan based on a previous initial realtime acquisition where anatomy, the point in the cardiac cycle and the point in the respiratory cycle are sampled many times per second. The gating times and acquisition durations are tailored to match a particular patient during a single patient session (i.e., the patient initial realtime acquisition of MR data and a further MRI are performed without the patient leaving). The relative position in the cardiac and respiratory cycles, using any form of cardiac and respiratory monitoring tools, is associated with each frame in an initial realtime MR acquisition. Such monitoring tools could include, but would not be limited to, peripheral plethymographs or ECG leads; pneumatic bellows or MR position measurements (e.g. navigator echoes).

Once the specific cardiac and respiratory phase are associated with each image in a realtime MR data set, a rapid analysis on the realtime image set is performed to determine initial times and durations over which certain specified criteria are satisfied. The initial times with the cardiac and respiratory cycles will be used to set initial timing values in the subsequent MR scan and the determined duration will be used to guide the choice of parameters which dictate the length over which image data is acquired.

Importantly, cardiac and respiratory information are collected in conjunction with realtime MR imaging and the physiological data is used in conjunction with the anatomic or spatial information to identify the correct gating times in the cardiac and respiratory cycles as well as the optimal acquisition durations with each of these cycles.

DETAILED DESCRIPTION OF THE INVENTION

Figure 1:
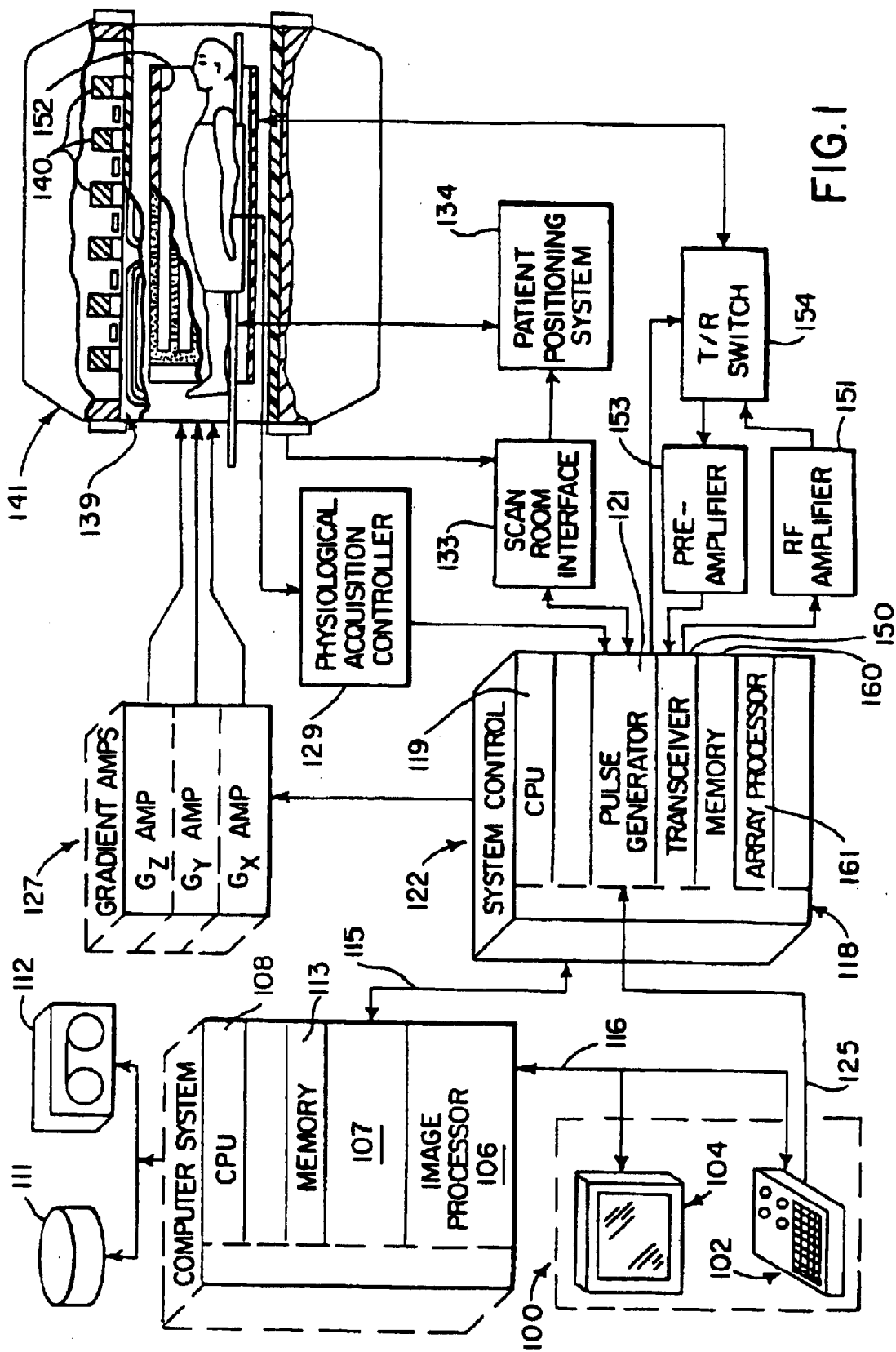
FIG. 1 is block diagram of a system according to the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes attached to the patient, peripheral plethymographs, pneumatic bellows or other monitoring tools. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a surface coil) to be used in either the transmit or receive mode.

The NMR signals picked up by the RF coil 152 are digitized by the transceiver module 150 and transferred to a memory module 160 in the system control 122. When the scan is completed and an array of raw k-space data has been acquired in the memory module 160. This raw k-space data may be rearranged into separate k-space data arrays for each cardiac phase image (or other images) to be reconstructed, and each of these is input to an array processor 161 which operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104. For a more detailed description of the transceiver 150, reference is made to U.S. Pat. Nos. 4,952,877 and 4,992,736 which are incorporated herein by reference. More details about various aspects of the system can be found in U.S. Pat. No. 6,144,200, hereby also incorporated by reference, whereas the description that follows will concentrate on features that are new.

Figure 2:
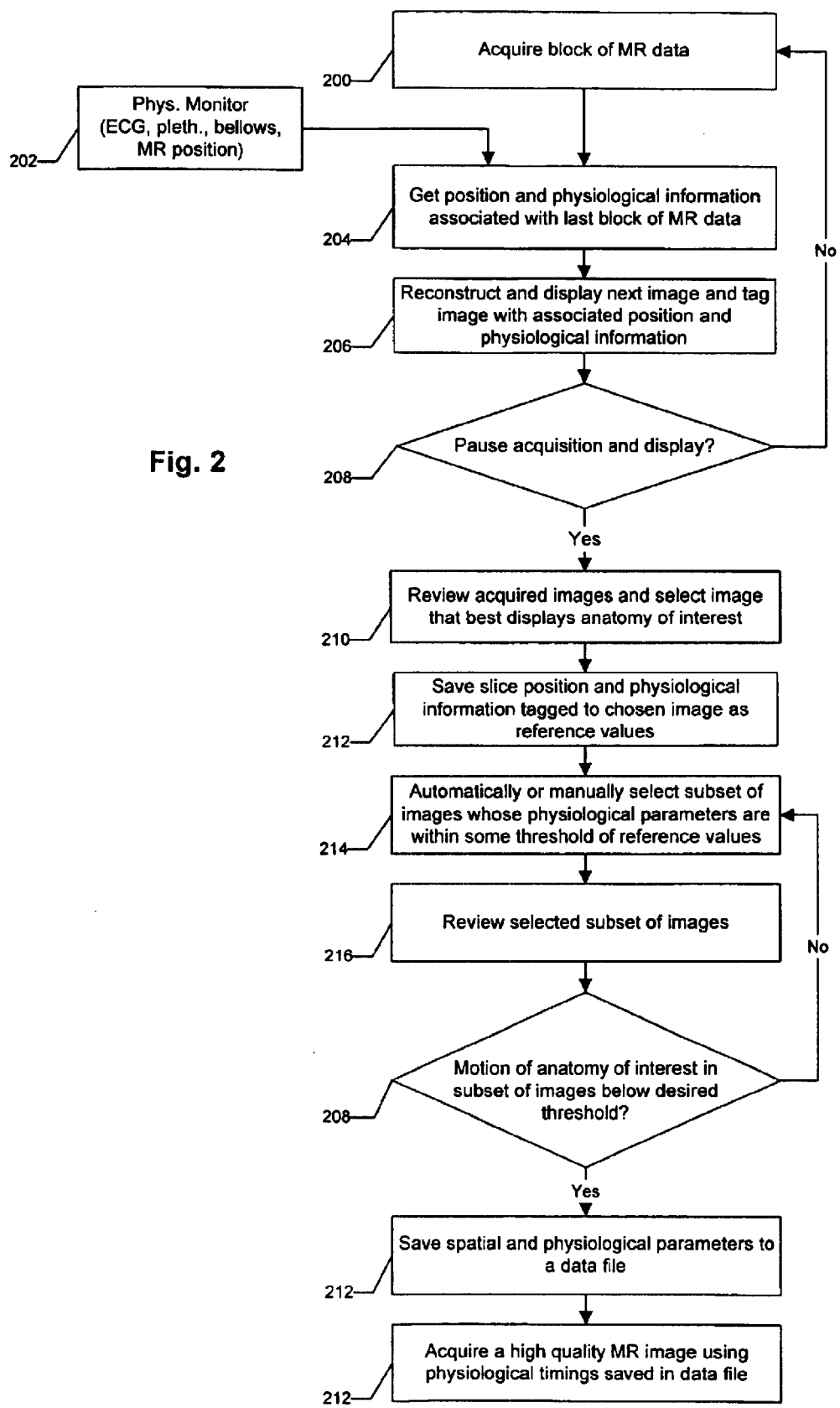
FIG. 2 is a simplified flow chart of the method of the present invention.

Turning now to FIG. 2, the process of the present invention is shown in a flow chart. At block 200, a block or set of MR data is obtained. This is one of an initial MR series done on the anatomy of interest of a particular patient. At block 202, a physiological monitor supplies data from ECG signals from electrodes attached to the patient, peripheral plethymographs, pneumatic bellows, MR position measurements (e.g., navigator echoes) and/or other monitoring tools. At block 204, the position/physiological information (i.e., values of the position/physiological functions) are associated with a given block of MR data (i.e., one frame in a series). At block 206, the image from that block and the associated position and physiological information will be displayed.

At block 208, a decision is made as to whether a sufficient initial MR series has been completed. A medical person may decide that sufficient data has been collected for the initial MR series. Alternately, a computer program analyzing the data may automatically indicate that sufficient data has been collected. A further alternative is that the program sets some parameters for the initial data collection, but the medical person may interactively adjust the criteria for initial data collection. At any rate, if decision block 208 determines that more data is needed, control goes back to block 200.

If sufficient initial data has been collected, block 208 indicates that the initial acquisition is sufficient, further acquisition of MR data is halted and block 210 is reached. At block 210, the acquired images are reviewed and the images that best display the anatomy of interest is selected.

As discussed above in connection with block 208, this review can be done by a medical person, a computer program, or, more preferably, a medical person interacting with a computer program. For example, if 100 frames of MR images and corresponding physiological data are collected, a computer program may select ten frames for the medical person to choose from. The medical person would then choose one or more of the frames. Note that the selection of, for example, three sequential frames as showing an anatomy of interest would indicate that the acquisition time used during a further MRI scan can have a duration as long as the three frames.

At block 212, the slice position and physiological information are saved as the selected or reference values. For example, a preferred image that best illustrates a feature of interest for the particular patient might be 40 ms after a given part of the patient's cardiac cycle. If the same feature of interest is well displayed by the two frames that sequentially follow the 40 ms frame, a good gating time would be 40 ms after the given part of the cardiac cycle and a good acquisition duration would be the time corresponding to the three frames.

Blocks 210 and 212 are an initial pass of the images, but block 214 may further review the images and select a subset with physiological parameters within some threshold of reference values. As discussed for other steps, this review can be done by a medical person, a computer program, or, more preferably, a medical person interacting with a computer program. The subset of images selected by block 212 may then be further reviewed, preferably by a medical person, at block 214, which leads to block 216 where a test is performed to determine if the motion of the anatomy of interest in the subset of images is below a desired threshold. If not, block 216 leads back to block 212.

When block 216 indicates that the motion is below the threshold, the spatial and physiologic function values or parameters are saved to a data file.

At block 222 a further MR imaging is performed, this time using the gating times and acquisition durations relative to the physiologic data saved. Referring back to the example where a feature of interest is well displayed by the three sequential frames that starting 40 ms after a particular part of the patient's cardiac cycle, this further MRI is performed using a gating time 40 ms after the given part of the cardiac cycle and an acquisition duration per cardiac cycle corresponding to the time interval of the three frames.

Note that the initial MRI and the further MRI are preferably and advantageously performed during a single patient session.

A specific example performed of the present invention will now be discussed. A version of the realtime imaging system was implemented on a 1.5T GE CVi Signa. Spiral readouts with a TR of 50 ms and 3 interleaves per image (~2 mm in-plane resolution) were used. Images were reconstructed after each new interleaf using a sliding window reconstruction resulting in a reconstructed frame rate of approximately 20 frames per second (fps). The current respiratory position (as measured by a bellows) and the elapsed time from the last cardiac trigger (as determined by ECG or plethysmograph) were sampled and saved with the realtime data. The realtime image review was modified so that a visual display of the respiratory and cardiac state for the current frame are shown. For any individual frame in the realtime image set, the parameters relating to the spatial position, slice orientation, cardiac and respiratory phases could then be saved to a file. A magnetization-preparation imaging sequence with spiral readouts was modified to import these parameters for scans of the root of the left (LCA) or right (RCA) coronary artery at the specified spatial position and physiological state. A long echo time (TE=105 ms) was used to emphasize blood signal relative to the surrounding myocardium. These scans were acquired at higher resolution (1.1 mm using 12 interleaves) than the realtime scans (~2 mm). Motion compensation using a diminishing variance algorithm as in patent 5,427,101 tuned to the identified respiratory phase was used for respiratory compensation.

Figure 3:
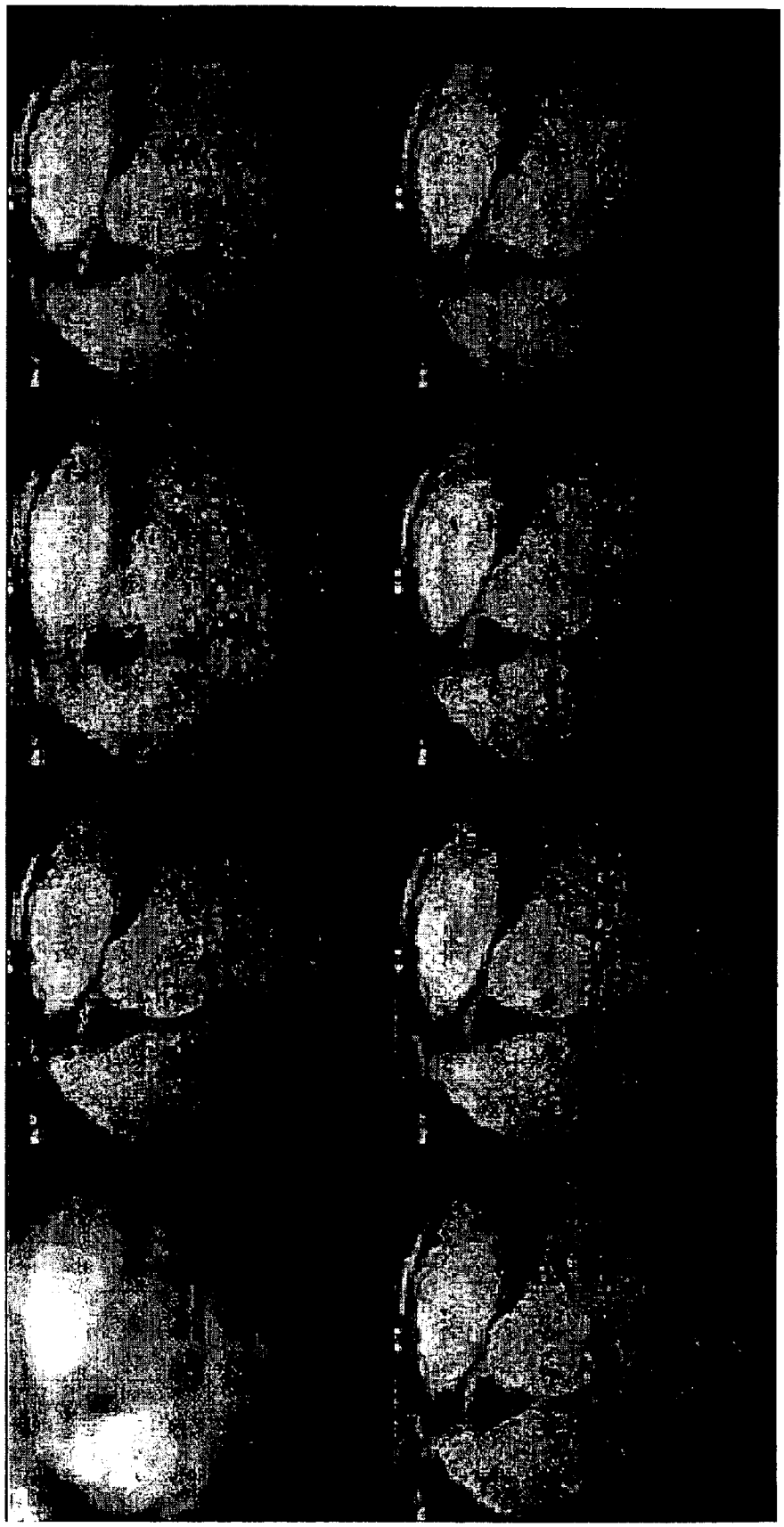
FIG. 3 are eight photomicrographs in a four column, two row arrangement and that will be used to explain the invention.

The eight photomicrographs of Images of the RCA in FIG. 3 going from left to right in the top row are a realtime frame, a magnetization-prepared image (note the greater clarity of the RCA), an image triggering 50 ms early, and an image triggering 50 ms late. The lower row of FIG. 3 show from left to right images corresponding to acquisition windows of 30, 60, 90 and 120 ms.

To examine the effect of readout duration, multiple images at the specified location were obtained with an increasing number of spiral interleaves (1 to 4) acquired per TR. The time for excitation/acquisition of one interleaf of data was 30 ms resulting in acquisition windows ranging from 30 ms to 120 ms within each TR. The number of signal averages was increased to keep the total scan time the same for all scans. Acquisitions were cardiac gated to every heartbeat with the delay time set based on the saved prescription data. All image frames from the realtime localization scan were saved and the motion of the artery of interest was determined using a known motion tracking algorithm.

Accurate prescription of location, cardiac and respiratory phase was consistently achieved by saving the associated parameters from the realtime study. The importance of accurate timing within the cardiac cycle is illustrated in FIG. 3 where a frame of the realtime study whose parameters were saved is shown at the left of the top row. Just to the left of that is the higher resolution scan of the RCA acquired using the saved parameters. The two images to the left of that images at the same slice position as the high resolution scan, but with cardiac delays 50 ms less than or greater than with the high resolution scan. A noticeable degradation of image quality is seen. Scans acquired using 1 to 4 interleaves per heartbeat, corresponding to data acquisition durations ranging from 30 to 120 ms respectively are shown in the lower row of FIG. 3. A slow degradation in image quality is seen with increasing acquisition durations.

Figure 4:
FIG. 4 are five photomicrographs in a single row and that will be used to explain the invention.

Similar images for the LCA are shown in FIG. 4 arranged in a row of five labeled a to e. FIG. 4a shows the selected frame of the realtime study and FIG. 2b-e show scans acquired using readout durations ranging from 30 to 120 ms. A more rapid degradation in image quality of the LCA (arrow) with increasing acquisition duration can be seen in the LCA.

Figure 5:
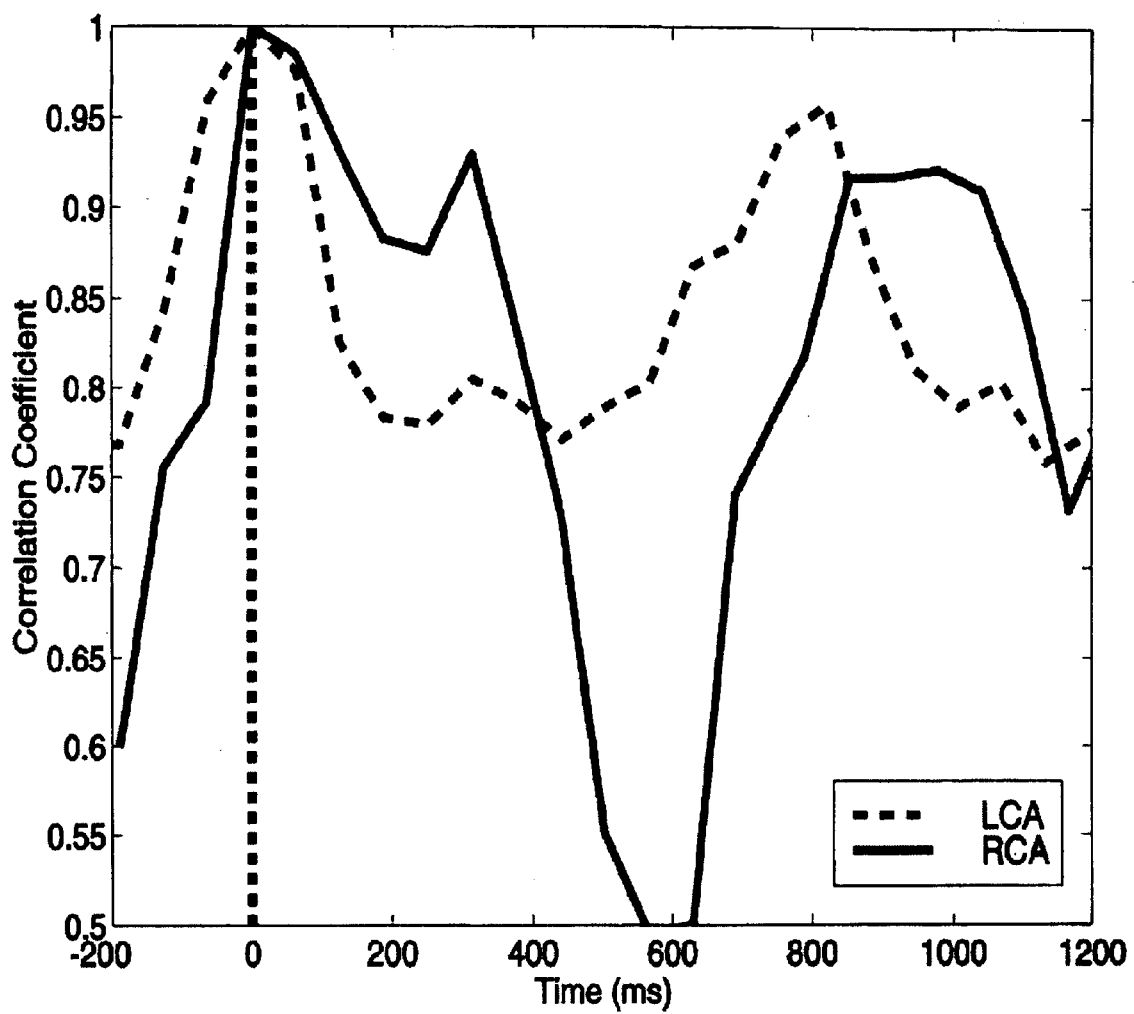
FIG. 5 shows a graph of correlation coefficients for the arteries.

The correlation coefficient from the motion tracking routine gives a relative measure of how consistently the coronary artery is visualized throughout the cardiac cycle. Larger values of the correlation coefficient indicate better visualization. FIG. 5 plots the correlation coefficient as a function of the relative time from the chosen trigger time (time t=0) for both the RCA and LCA over a typical cardiac cycle. The importance of accurate timing can be seen by how quickly the correlation coefficient drops at times prior to the chosen trigger time (and seen by the lack of visualization of the artery in FIG. 3 (third image from left in top row). The effect of acquisition duration can be evaluated by noting that the value for the RCA remains higher longer than for the LCA.

Note that normally the magnitude of motion in the RCA is greater than the LCA but in the example the LCA moved out of the imaging plane, causing a drop in the correlation coefficient and a subsequent loss of image quality with increasing readout durations.

Locating and timing imaging in and around the heart is critical due to motion arising from cardiac and respiratory cycles. The use of physiological and motion information through a realtime imaging interface allows rapid, accurate identification of appropriate scan positions, timings and acquisition windows on a subject-by-subject basis. This allows for robust acquisitions which are tailored to the patient.

This is quite a contrast with techniques that are based on a given formula (e.g., particular part of the cardiac cycle) regardless of the special characteristics of a given patient.

What is claimed is:

1. A method of magnetic resonance imaging (MRI), the steps comprising:
    subjecting an anatomy of interest to an initial realtime MRI to acquire an initial series of images;
    simultaneously with the subjecting, monitoring the values of at least one physiological function related to movement of the anatomy of interest or a portion thereof;
    associating with each image in the initial series, the corresponding value of the physiological function;
    selecting images from among the initial series where the anatomy of interest appears;
    selecting gating times and acquisition durations using the value of the physiological function associated with the selected images; and
    forming an output image from further MRI of the anatomy of interest using the selected gating times and acquisition durations and dependent on the value of the physiological function.

2. The method of magnetic resonance imaging (MRI) of claim 1 wherein the output image at least one member of the group consisting of: a two-dimensional (2D) with a higher signal-to-noise ratio than the images of the initial series, a 2D image with higher spatial resolution, and a three-dimensional (3D) image.

3. The method of magnetic resonance imaging (MRI) of claim 2 wherein the monitoring step is performed by a tool selected from the group consisting of: a peripheral plethymograph, ECG leads, pneumatic bellows, and MR position measurements.

4. The method of magnetic resonance imaging (MRI) of claim 2 wherein the step of associating with each image in the initial series includes associating the values of at least two physiological functions to each image.

5. The method of magnetic resonance imaging (MRI) of claim 4 wherein the physiological functions are cardiac and respiratory functions.

6. The method of magnetic resonance imaging (MRI) of claim 4 wherein the step of selecting gating times and acquisition durations uses the values of both physiological functions associated with the selected images.

7. The method of magnetic resonance imaging (MRI) of claim 6 wherein the step of forming an output image from further MRI of the anatomy of interest uses the selected gating times and acquisition durations and is dependent on the values of the at least two physiological functions.

8. The method of magnetic resonance imaging (MRI) of claim 2 wherein the step of selecting images from among the initial series is performed at least partly automatically by a processor that excludes some images.

9. The method of magnetic resonance imaging (MRI) of claim 2 wherein the anatomy of interest is part of a patient and wherein both the initial realtime MRI and the further MRI are performed during a single patient session.

10. A method of magnetic resonance imaging (MRI), the steps comprising:
    subjecting an anatomy of interest to an initial realtime MRI to acquire an initial series of images;
    simultaneously with the subjecting, monitoring the values of at least one physiological function related to movement of the anatomy of interest or a portion thereof;
    associating with each image in the initial series, the corresponding value of the physiological function;
    selecting images from among the initial series where the anatomy of interest appears;
    selecting gating times using the value of the physiological function associated with the selected images; and
    forming an output image from further MRI of the anatomy of interest using the selected gating times and acquisition durations and dependent on the value of the physiological function, and wherein the output image at least one member of the group consisting of: a two-dimensional (2D) with a higher signal-to-noise ratio than the images of the initial series, a 2D image with higher spatial resolution, and a three-dimensional (3D) image.

11. The method of magnetic resonance imaging (MRI) of claim 10 wherein the anatomy of interest is part of a patient and wherein both the initial realtime MRI and the further MRI are performed during a single patient session.

12. The method of magnetic resonance imaging (MRI) of claim 11 wherein the step of associating with each image in the initial series includes associating the values of at least two physiological functions to each image.

13. The method of magnetic resonance imaging (MRI) of claim 12 wherein the physiological functions are cardiac and respiratory functions.

14. The method of magnetic resonance imaging (MRI) of claim 12 wherein the step of selecting gating times uses the values of both physiological functions associated with the selected images, and wherein the step of forming an output image from further MRI of the anatomy of interest uses the selected gating times and is dependent on the values of the at least two physiological functions.

15. The method of magnetic resonance imaging (MRI) of claim 14, further comprising the step of:
    selecting acquisition durations using the values of the at least two physiological functions associated with the selected images; and
    wherein the step of forming of the output image from further MRI of the anatomy of interest uses the selected acquisition durations and is dependent on the values of the at least two physiological functions.

16. A system for magnetic resonance imaging (MRI), comprising:
    an MRI device operable to subject an anatomy of interest to an initial realtime MRI to acquire an initial series of images;
    a physiological monitor operably connected to the anatomy of interest and operable to, simultaneous with the initial realtime MRI, monitor the values of at least one physiological function related to movement of the anatomy of interest or a portion thereof;
    means for associating with each image in the initial series, the corresponding value of the physiological function;

means for selecting images from among the initial series where the anatomy of interest appears;

means selecting gating times and acquisition durations using the value of the physiological function associated with the selected images; and means forming an output image from further MRI of the anatomy of interest using the selected gating times and acquisition durations and dependent on the value of the physiological function.

17. The system for magnetic resonance imaging (MRI) of claim 16 wherein the anatomy of interest is part of a patient and wherein the means forming an image is operable to perform the further MRI during a single patient session in which the initial MRI is also done.

18. The system for magnetic resonance imaging (MRI) of claim 17 wherein the physiological monitor is operable to monitor a function selected from the group consisting of: cardiac function and respiratory function.

19. The system for magnetic resonance imaging (MRI) of claim 17 further comprising a second physiological monitor operably connected to the anatomy of interest and operable to, simultaneous with the initial realtime MRI, monitor the values of a second physiological function related to movement of the anatomy of interest or a portion thereof; wherein the means for associating with each image in the initial series, the corresponding value of the physiological function also associates the corresponding value of the second physiological function; and wherein the means for selecting gating times and acquisition durations using the value of the second physiological function associated with the selected images; and wherein the means forming an output image from further MRI of the anatomy of interest using the selected gating times and acquisition durations dependent on the value of the second physiological function.

20. The system for magnetic resonance imaging (MRI) of claim 16 wherein the means for producing an output image produces at least one member of the group consisting of: a two-dimensional (2D) with a higher signal-to-noise ratio than the images of the initial series, a 2D image with higher spatial resolution, and a three-dimensional (3D) image.

* * * * *